(12) United States Patent
Tiefenthaler

(10) Patent No.: US 6,818,886 B2
(45) Date of Patent: Nov. 16, 2004

(54) DETECTION METHOD

(75) Inventor: Kurt Tiefenthaler, Zürich (CH)

(73) Assignee: Artificial Sensing Instruments ASI AG, Zurich (CH)

( * ) Notice: Subject to any disclaimer, the term of this patent is extended or adjusted under 35 U.S.C. 154(b) by 0 days.

(21) Appl. No.: 10/344,186

(22) PCT Filed: Aug. 9, 2001

(86) PCT No.: PCT/CH01/00487

§ 371 (c)(1), (2), (4) Date: Feb. 7, 2003

(87) PCT Pub. No.: WO02/12866

PCT Pub. Date: Feb. 14, 2002

(65) Prior Publication Data

US 2003/0168587 A1 Sep. 11, 2003

(30) Foreign Application Priority Data

Aug. 9, 2000 (CH) .............................................. 1558/00

(51) Int. Cl.[7] .............................................. H01J 49/00
(52) U.S. Cl. ...................................... 250/282; 356/128
(58) Field of Search ........................... 250/282; 356/128

(56) References Cited

U.S. PATENT DOCUMENTS

| | | | | |
|---|---|---|---|---|
| 4,815,843 A | * | 3/1989 | Tiefenthaler et al. | ....... 356/128 |
| 5,071,248 A | * | 12/1991 | Tiefenthaler et al. | ....... 356/128 |
| 5,479,260 A | * | 12/1995 | Fattinger | .................... 356/481 |
| 5,738,825 A | * | 4/1998 | Rudigier et al. | ......... 422/82.11 |
| 5,955,729 A | | 9/1999 | Nelson et al. | |

OTHER PUBLICATIONS

WO 99/13320, Optical Sensor and Optical Method for Characterizing a Chemical or Biological Substance, Publication Date Mar. 18, 1999.

* cited by examiner

*Primary Examiner*—John R. Lee
*Assistant Examiner*—Erin-Michael Gill
(74) *Attorney, Agent, or Firm*—Rankin, Hill, Porter & Clark LLP

(57) ABSTRACT

A method for detecting a substance or substances in a sample or in a matrix of samples combining detection methods that are, on the one hand, based on direct detection with integrated optical (bio)chemo-sensitive waveguide grating structures and, on the other hand, based on a mass-spectrometric detection effected by way of a desorption process. The method permits an increase in detection security and/or detection sensitivity.

19 Claims, No Drawings

DETECTION METHOD

BACKGROUND OF THE INVENTION

Optical chemo- and biosensors based on integrated optical (bio)chemo-sensitive or (bio)chemo-functional waveguide grating structures permit the marking-free detection of (bio) molecular interactions in real time and are described in the literature (see e.g. U.S. Pat. Nos. 4,815,843 and 5,071,248). However marking detections are also possible (see e.g. WO 99/13320).

The method according to the invention not only represents a detection method, but also a separation technology since the substance to be tested or the substances to be tested, of the sample or of the matrix of samples, are separated in that the substance(s) binds(bind) onto the (bio)chemo-sensitive layer(s) located on the sensor chip.

A marking-free detection is effected in a first step, as is described in U.S. Pat. Nos. 4,815,843; 5,071,248; 5,738,825; 5,479,260 and EP 0,482,377. Subsequently, the substance (or parts (fragments) thereof) to be detected and binding onto the (bio)chemo-sensitive layer on the sensor chip is analysed more exactly in a mass spectrometer with a desorption step (and ionisation step).

SUMMARY OF THE INVENTION

The present invention describes detection systematics in which integrated optical chemo- and biosensorics (with or without marking technology (index marker, fluorescence marker, luminescence marker, phosphorescence marker, enzyme marker)) are combined with mass spectroscopy with a desorption step (and ionisation step). The desorption step releases the molecules from the surface of the sensor chip. The mass spectrometer measures the masses and/or the degree of ionisation of the molecules (atoms, ions, biomolecules, fragments etc.). The present invention thus creates detection systematics that further increases the detection sensitivity as well as the security of detection.

DETAILED DESCRIPTION OF THE PREFERRED EMBODIMENTS

Integrated optical chemo- and biosensors are above all to be understood as those integrated optical sensor chips, which are based on (bio)chemo-sensitive or (bio)chemo-functional waveguide grating structures. A waveguide grating structure consists of at least one waveguide grating structure unit (with or without reference waveguide grating structure unit) or of at least one sensor location (with or without reference sensor location). A waveguide grating structure comprises at least one grating location). A waveguide grating structure unit comprises at least one grating, but may however also have at least one in-coupling grating and one out-coupling grating. The in-coupling grating and the out-coupling grating may have the same or different grating periods. A waveguide grating structure may also consist of only one large (uni-diffractive or multi-diffractive) grating. A waveguide grating structure may contain several sensor pads (two, three, four etc.) lying next to one another and/or in one another and/or over one another, in order e.g. to excite a TE-wave (preferably in the base mode) in the forwards and rearwards direction and a TM-wave (preferably in the base mode) in the forwards and rearwards direction.

Chiefly highly-diffractive materials are considered with regard to waveguiding films, such as $TiO_2$, $Ta_2O_5$, $ZrO_2$, $HfO_2$, $Si_3N_4$ etc. The waveguide (the waveguide structure) is mainly a monomode structure, thus carries only the base modes TE0 (TE=transversal electrical, mode number m=0) and TM0 (TM=transversal magnetic, mode number m=0). A waveguide structure may contain several layers, wherein preferably of these at least one layer is highly diffractive. The waveguide (the waveguide structure) may also be light-absorbing. At the same time, the absorbing material may be embedded into a layer or into the substrate, or also an absorbing layer or an absorbing substrate may be present. An absorbing layer may, for example, be a metal layer (chromium, aluminium, nickel, gold, silver etc).

Apart from (bio)molecular binding partners (such as e.g. antibodies, antigenes, receptors, peptides, phages, "single-stranded" DNA(RNA)-sections, genes, gene sections, targets, proteins, binding proteins, enzymes, inhibitors, nucleic acids, nucleotides, oligonucleotides, SNP, allergens, pathogens, carbohydrates, metabolites, hormones, active ingredients, molecules with low molecular weight, lipids, signal substances etc.) one may also apply "molecular imprinted polymers" (such as plastic antibodies, plastic antigenes etc.) or (living) cells as (bio)chemo-functional layers. The binding procedures (or the (bio)chemical reactions) may also be effected here at the surface, in the volume or on the surface as well as in the volume of the (bio)chemo-functional layer.

The (bio)chemo-functional layer may at the same time lie on a (uni-diffractive or multi-diffractive) waveguide grating or between two (uni-diffractive or multi-diffractive) waveguide gratings (of the same or different grating period and/or modulation). In the later case, the two gratings are construed as belonging to one waveguide grating structure unit. In the case of scatter light measurements or fluorescence, luminescence or phosphorescence measurements, the (bio)chemo-functional layer may also be located next to the waveguide grating. The (bio)chemo-functional layers may also cover a large waveguide grating in an array-like (matrix-like or circular) manner, without the (bio)chemo-functional layers overlapping. The (bio)chemo-functional layers (signal layer and/or reference layers) define the sensor locations. A passivation material that, where appropriate, suppresses non-specific binding (NSB) may (need not) be located between the (bio)chemo-sensitive layers.

A (removable) sample accommodation device (e.g. (removable) cuvette, a (removable) well or a (removable) through-flow or capillary cuvette) or an array of sample accommodation devices may be located above the (bio) chemo-sensitive waveguide grating structure. The well is mostly a component of a well plate. The sample accommodating device may, however, also be incorporated into the waveguide grating structure. Photolithography, laser ablation, (hot) embossing technology or plastic (hot) embossing technology, and injection molding technology are suitable as manufacturing methods. The recesses in the substrate act as wells. A (channel-like) recess with a cover plate (provided with supply and removal bores) may act as a through-flow cuvette, a (channel-like) recess with a (part) covering may act as a capillary cuvette. The waveguide grating structure need not necessarily be provided with a sample-accommodating device. For example, the samples may be deposited with a pipetting robot in the form of drops. During measurement the injection needles or pipette tips of the pipetting robot may (or may not) remain in contact with the sample droplet deposited on the sensor chip.

The inner wall of a through-flow channel of a lab-on-chip may be provided with a (bio)chemo-sensitive waveguide grating structure. If the cover plate of the through-flow channel is removed, then the (bio)molecules accumulated on the (bio)chemo-sensitive waveguide grating structure may be brought to desorb into the upper half space by way of a desorption process (e.g. LDI-process or MALDI-process). Preferably, no sample fluid is located in the through-flow channel during the desorption procedure. However, one may also operate without the removal of the cover plate. The MALDI-matrix may, for example, be supplied via a sample loop. The lab-on-chip or the cover plate is transparent to the laser radiation that triggers the desorption. The desorbed (bio)molecules migrate along the through-flow channel and at the end get into the vacuum of the mass spectrometer. If working in the liquid phase, the outlet of the through-flow channel may, for example, be connected to an electrospray-ionization part of a mass spectrometer (quadrupole-, tandem-, time-of-flight mass spectrometer etc.).

It is not good to add plastic parts to the vacuum of the mass spectrometer since plastic parts desorb material into the vacuum. For this reason it is also advantageous to use sensor chips on glass substrates. The photo-lithographic manufacture of gratings in glass (with wet or dry etching) or the manufacture of the gratings with glass embossing technology is known from the literature. Gratings in plastic substrates may, for example, be manufactured with (hot) embossing technology or injection molding technology (with or without compression step(s)).

The direct detection of a binding in the case that the (bio)chemo-sensitive layer is located on the grating is effected, for example, by way of an in-coupling angle measurement or an out-coupling angle measurement or a wavelength measurement (see U.S. Pat. No. 4,815,843) or an interferometric measurement (see U.S. Pat. No. 5,479,260), and in the case that the (bio)chemo-sensitive layer is located between two waveguide gratings (of the same or different grating period) is effected by way of an interferometric measurement (see Biosensors & Bioelectronics 6 (1991), 215–225, European Patent 0 226 604 B1). Interferometric measurements may, for example, be based on the Mach-Zehnder principle, wherein both light paths may be guided separated from one another via the in-coupling grating and out-coupling grating. One light path sees the (bio)chemo-functional layer, the other light path sees another or inert or even no (bio)chemo-functional layer. Such measuring technology has been described by R. G. Heideman et al., "Development of an Optical Waveguide Interferometric Immunosensor" Proceedings Eurosensors 4, Karlsuhe, 1990. In our case a transparent substrate is preferred in order to permit light incidence from the substrate side.

Another measuring technology is based on the measurement of emission light (fluorescence, luminescence, phosphorescence light) on waveguide (grating) structures in combination with a direct measurement. With this, a layer of the waveguide structure (consisting of one or more layers) and/or a layer between the waveguiding film and the substrate and/or a layer between the waveguiding film and cover (or (bio)chemo-functional layer) and/or a layer on the underside of the substrate and/or the substrate itself is light-emitting (fluorescence, luminescence, phosphorescence light) on excitation with light (with a wide and/or narrow excitation spectrum). This layer may, for example, be a polymer layer (or a solid-state-like layer or a glass-like layer) with a (high) intrinsic fluorescence or with embedded emission light molecules (fluorescence, luminescence, phosphorescence molecules). The emission light wavelength is different from the excitation wavelength. The method systematics are based on the incident angle scanning mode or on a wavelength scanning mode (with a matchable light source), wherein in the beam path between the sensor chip and the detector there is located a wavelength filter (blocking the excitation light, transparent to the emission light). A beam splitter may also be located between the sensor chip and the detector, wherein then the wavelength filter is preferably in the beam path between the beam splitter and detector. The excitation light may, for example, be incident onto the sensor chip ((bio)chemo-functional waveguide grating structure) via the beam splitter. The excitation light may also be incident obliquely from the substrate side or obliquely from the cover side onto the sensor chip, wherein the beam splitter may or may not be present. The emission light may also (preferably) be measured in a direction that does not correspond to the reflection direction of the excitation light beam. The incident light beam on fulfilling the in-coupling equation produces a guided light wave, but may also excite emission light that, by way of the led mode, is directly or indirectly (resonance-like) intensified and/or shifted with respect to center of intensity. The (radiated and/or out-coupled) emission light of the emission layer is imaged onto the detector with a lens (lens system). The out-coupled light of the excitation wave may or may not be incident onto the imaging lens. The out-coupled emission light may or may not be incident onto the imaging lens. The measuring systematics represents a combination of direct measurement with fluorescence (luminescence, phosphorescence) measurement. Since with the wavelength scanning mode the (excitation) wavelength is shifted, the excitation spectrum must be sufficiently broad. Light-emitting mode-beating patterns (between the TE mode and TM mode) and light-emitting interferometric patterns with and without (uni-diffractive or multi-diffractive) gratings with scanning operation (incident angle scanning mode or wavelength scanning mode) or without scanning operation (excitation of the modes TE and/or TM with planar or slightly focussed waves) may be measured with the application of polarizer (e.g., 45° polarizer) located between the sensor chip and the detector in the case of interference of TE-light and TM-light, and with the application of the mentioned wavelength filter at the point in time of mode excitation, wherein the modes of the excitation wavelength are produced via grating in-coupling. A binding reaction (or mass accumulation) or chemical reaction (change of the complex refractive index) on the (bio)chemo-functional layer that is located on and/or next to the grating, changes the period of the interference pattern.

In place of removing the well plate, the well plate may also be brought into contact with the vacuum such that only the sensor locations come into contact with the vacuum, but not the sample plate. This is effected by way of the fact that hollow cylinders are introduced into the wells, which, amongst one another, are again connected to one another in a vacuum-tight manner. The above-complicated design becomes invalid if, however, the wells are introduced into the waveguide grating.

There are, however, also sample plates of glass or plastic, which likewise are subjected to the vacuum.

One advantageous embodiment of an integrated optical (IO) sensor chip or IO-sensor chip plate is a micro-plate with, for example, 24, 48, 96, 384, 1536 wells or a sensor chip array (e.g. micro-array) with any number of sensor locations. Microplates are described in U.S. Pat. No. 5,738,825 and WO 99/13320. In WO 99/13320 it is further described how temperature-compensated marking-free detection technology functions. With the micro-array the (bio)chemo-sensitive layers are advantageously deposited with a spotter or a contact-printing robot in a matrix-like (or also circular) manner. A micro-array—or also generally a waveguide grating structure—may comprise a (location-dependent or also non-location dependent) absorbing or also non-absorbing waveguide. A micro-array—or also generally a waveguide grating structure—may have a large extended (uni-diffractive or multi-diffractive) grating with an array of (bio)chemo-functional layers or also consist of an array of (bio)chemo-functional waveguide grating structure units. A waveguide grating structure unit in each case is at least partly covered by a (bio)chemo-sensitive layer. The microarray may (need not) be provided with a (removable) fluid receptacle (cuvette, well, through-flow cell, capillary cuvette etc.).

The (bio)chemo-sensitive ((bio)chemo-functional) layers (signal layers and/or reference layers) are preferably deposited with a spotter or contact-printing robot or a liquid handler, wherein a linker-layer or also a (absorbing or nor-absorbing) distance layer may be located between the (bio)chemo-functional layer and the waveguide grating structure. Micro-arrays are, for example, applied in genomics or proteomics. In genomics the (bio)chemo-functional layers are, for example, gene sections, nucleic acids, single stranded DNA (RNA), single nucleotide polymorphism (SNP), etc. In proteomics, the (bio)chemo-functional layers are, for example, proteins, phages, etc.

The particular advantage of grating-based integrated optical chemo- and biosensors is their ability to be automised, since each sensor location is simply addressable via diffraction. Sensor locations may be illuminated after one another or simultaneously. Simultaneous illumination of the sensor locations may be effected with several beams or with a diverged beam. The beam may contain a wavelength or several (discrete or continuous) wavelengths.

A MALDI step (matrix assisted laser desorption ionisation) may serve as a desorption/ionisation step for the mass spectrometer. This desorption process produces molecules in the ionised condition. The MALDI matrix is not compellingly required in some applications. A laser desorption and ionisation (LDI) may also take place without a MALDI matrix or with a different desorption and ionisation source. Where appropriate, one adds yet a separate ionisation step.

Various MALDI matrixes are used according to the analyte. The MALDI matrices are described in the literature. Typical MALDI matrices are derivatives of the cinnamic acid, alpha-cyano-4-hydroxycinnamic acid, gentisic acid, dithranol, sinapinic acid, etc.

The desorption process may, however, also be triggered by an ion source (or ion beam), an atomic source (or atomic beam), an electron source (or electron beam), an X-ray source (or x-ray beam), etc.

A TOF (time of flight) mass spectrometer may be applied. Other mass spectrometers are magnetic sector mass spectrometers, ion trap mass spectrometers, quadrupole mass spectrometers, tandem mass spectrometers, dual quadrupole mass spectrometers, triple quadrupole mass spectrometers, Fourier transform ion cyclotron resonance mass spectrometers, etc.

The (bio)chemo-sensitive waveguide grating structure may be applied in a pre-chamber of the mass spectrometer. This pre-chamber is then evacuated. The chamber of the mass spectrometer remains under a vacuum. If the pre-chamber is evacuated then the sluice between the pre-chamber and the chamber may be opened. However, the (bio)chemo-sensitive waveguide grating structure may be applied into the chamber of the mass spectrometer and the chamber subsequently be evacuated.

The mass spectrometer measures, for example, in the mass spectrum the ratio of m/z of mass to charge. The peak height of a peak in the mass spectrum is a measure of the quantity of analytes that are ionised and detected by the mass spectrometer. The sensor chip (e.g. single-channel chip, multi-channel chip, microplate, microarray, lab-on-chip, disc chip, etc) is applied into the measuring device, then a vacuum is produced and, subsequently, the desorption process is activated. The desorbed molecules or ions are analysed in the mass spectrometer.

Liquid samples may be ionised via an electro-spray ionisation step (ESI) and subsequently led to the mass spectrometer.

The MALDI matrix may be deposited onto the sensor chip with a (bio)chemo-functional layer and possibly a substance to be detected, which is bonded thereon, in the liquid phase as well as in the gas phase.

The MALDI matrix is shot with a pulsed or non-pulsed laser (wavelength region: X-ray, gamma, UV, VIS, IR). Pulsed lasers are, for example, a nitrogen laser or a (Q-switched) Nd-YAG laser, where appropriate, with a frequency doubling, or frequency tripling or a frequency quadruplication, or an Erbium-YAG laser.

The laser beam or the sensor chip (the waveguide grating structure) may be displaced for traversing to a measuring location.

The laser beam that is responsible for the desorption may impinge the (bio)chemo-functional layer (with possibly bonded substance) from the substrate side as well as from the cover side. The incidence from the substrate side requires transparency of the substrate with respect to the laser wavelength. However, the laser beam responsible for the desorption may be coupled into the waveguide structure from the cover side or from the substrate side via a waveguide grating. With highly diffractive waveguiding films (or with a large difference in the refractive index between the substrate and the waveguiding film), as is known, the electromagnetic field strength of the evanescent wave reaching into the (bio)chemo-functional layer is particularly high. In this case the evanescent wave at least also takes part in the desorption.

With the (pulsed or non-pulsed) laser beam (with reduced power) responsible for the desorption it is also possible to make a direct detection (in real time or as an end-point measurement (with regard to the initial condition)) or to make a direct detection with a second control laser (e.g., HeNe laser or laser diode) or to follow the desorption procedure using a grating coupling principle (e.g., incident angle scanning mode, out-coupling angle scanning mode, wavelength scanning mode) or an interferometric principle. For this, one requires optics and detectors and measuring means (for the absolute measurement), as, for example, are described in a second patent application with the same priority by the company Artificial Sensing Instruments ASI AG. The detectors are preferably not located in a vacuum, but may also be located in a vacuum.

The MALDI matrix absorbs the laser light and with this triggers the desorption. If marking substances are present on the (bio)chemo-functional layer or on the accumulated substances to be detected, then the molecular weight (and the ionisation) of the marking substance or the desorbed marking substance fragments in the mass spectrum must be taken into account.

The advantage of the detection systematics according to the invention is that with the integrated optical chemo- and biosensorics there may be effected a rapid direct detection at several sensor locations (on a one-dimensional or two-dimensional array of sensor location) and subsequently in a vacuum at selected sensor locations there may be effected a more time-consuming, but more accurate mass-spectroscopic analysis on the bonded substance (or on parts thereof).

What is claimed is:

1. A method for detecting a substance or substances in a sample or in a matrix of samples, comprising the steps of:
   (a) separating the substance or substances to be detected from the sample or matrix of samples with one of an integrated optical (bio)chemo-sensitive sensor-chip plate, of an integrated optical (bio)chemo-sensitive micro-array and of an integrated optical (bio)chemo-sensitive lab-on-chip, wherein each of said integrated optical (bio)chemo-sensitive sensor-chip plate, of said integrated optical (bio)chemo-sensitive micro-array and of said integrated optical (bio)chemo-sensitive lab-on-chip comprises at least one (bio)chemo-sensitive waveguide grating structure unit or (bio)chemo-sensitive sensor location;
   (b) detecting during or after the separation the substance or the substances with the help of a light wave, said light wave having an evanescent field and being at least partly guided in a waveguide structure;
   (c) detecting the substance or the substances or substance parts on selected (biochemo-sensitive waveguide grating structure units or on selected (bio)chemo-sensitive sensor locations by desorption and ionization of the substance or the substances or the substance parts with the help of a mass spectrometer.

2. The method according to claim 1, wherein a (bio)chemo-sensitive layer at least partly covers the waveguide grating structure unit or the sensor location of a waveguide grating.

3. The method according to claim 1, wherein a (bio)chemo-sensitive layer covers a diffracting part of the waveguide grating structure unit.

4. The method according to claim 1, wherein a (bio)chemo-sensitive layer covers a non-diffracting part of the waveguide grating structure unit.

5. The method according to claim 1, wherein at least one of a waveguide grating and the waveguide grating structure unit contains a uni-diffractive waveguide grating.

6. The method according to claim 1, wherein at least one of a waveguide grating and the waveguide grating structure unit contains a multi-diffractive waveguide grating.

7. The method according to claim 1, wherein the waveguide grating structure unit consists of two waveguide gratings lying next to one another, both waveguide gratings belong to the same waveguide grating structure unit and the non-diffracting distance between the two waveguide gratings is part of the waveguide grating structure unit.

8. The method according to claim 1, wherein the waveguide grating structure unit consists of two part-waveguide grating structures lying next to one another and the non-diffracting distance between the two part-waveguide grating structures is part of the waveguide grating structure.

9. The method according to claim 1, wherein at least one of a waveguide grating and the waveguide grating structure contains a one-dimensional or two-dimensional array of sensor locations.

10. The method according to claim 1, wherein the sensor chip plate is a micro-plate.

11. The method according to claim 1, wherein at least one of the sensor chip plate, a micro-array, and the lab-on-chip comprises a glass substrate.

12. The method according to claim 1, wherein at least one of the sensor chip plate, a micro-array, and the lab-on-chip comprises a polymer substrate.

13. The method according to claim 1, wherein at least one of the sensor chip plate, a micro-array, and the lab-on-chip comprises a removable sample accommodating device or sample holder device.

14. The method according to claim 1, wherein at least one of the sensor chip plate, a micro-array, and the lab-on-chip comprises a sample accommodating device or a sample holding device of glass.

15. The method according to claim 1, wherein at least one of the sensor chip plate, a micro-array, and the lab-on-chip comprises a sample accommodating device or a sample holder device of polymer.

16. The method according to claim 1, wherein desorption and ionisation is effected by shooting with a pulsed laser.

17. The method according to claim 1, wherein a (bio)chemo-sensitive waveguide grating structure unit with accumulated analyte or a (bio)chemo-sensitive sensor location of a waveguide grating with accumulated analyte is provided with a MALDI matrix.

18. The method according to claim 1, wherein desorption and ionisation is effected via a MALDI step.

19. The method according to claim 1, wherein the mass spectrometer is a time-of flight (TOF) mass spectrometer or a quadrupole mass spectrometer.

* * * * *

UNITED STATES PATENT AND TRADEMARK OFFICE
CERTIFICATE OF CORRECTION

PATENT NO. : 6,818,886 B2
DATED : November 16, 2004
INVENTOR(S) : Tiefenthaler

It is certified that error appears in the above-identified patent and that said Letters Patent is hereby corrected as shown below:

Column 7,
Line 31, delete "(biochemo-sensitive" and insert -- (bio)chemo-sensitive --.

Signed and Sealed this

Twelfth Day of April, 2005

JON W. DUDAS
*Director of the United States Patent and Trademark Office*